United States Patent [19]

Kappler et al.

[11] 4,234,503
[45] Nov. 18, 1980

[54] METHOD OF PREPARING GAMMA AMINOPROPYL ALKOXY SILANES

[75] Inventors: Fritz-Robert Kappler, Troisdorf; Claus-Dietrich Seiler, Rheinfelden; Hans-Joachim Vahlensieck, Wehr, all of Fed. Rep. of Germany

[73] Assignee: Dynamit Nobel Aktiengesellschaft, Troisdorf, Fed. Rep. of Germany

[21] Appl. No.: 971,966

[22] Filed: Dec. 21, 1978

[51] Int. Cl.$^3$ .............................. C07F 7/10; C07F 7/18
[52] U.S. Cl. .................................................. 556/413
[58] Field of Search ................................ 260/448.8 R

[56] References Cited

U.S. PATENT DOCUMENTS

| | | | |
|---|---|---|---|
| 3,621,047 | 11/1971 | Golitz et al. | 260/448.8 R |
| 4,045,460 | 8/1977 | Kleinstück | 260/448.8 R |
| 4,064,155 | 12/1977 | Speier | 260/448.8 R |

Primary Examiner—Paul F. Shaver
Attorney, Agent, or Firm—Sprung, Felfe, Horn, Lynch & Kramer

[57] ABSTRACT

A process for preparing a gamma amino propyl alkoxy silane of the formula

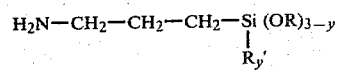

wherein R is an alkyl moiety of 1 to 4 carbon atoms, R' is methyl or phenyl, and y is 0, 1 or 2 which comprises contacting the corresponding gamma-chloropropyl alkoxy silane with ammonia under pressure at a temperature between 50° and 90° C. while stirring the reaction mixture.

10 Claims, No Drawings

METHOD OF PREPARING GAMMA AMINOPROPYL ALKOXY SILANES

The subject matter of the present invention is a method of preparing γ-aminopropylalkoxysilanes by reacting γ-chloropropylalkoxysilanes and ammonia.

The reaction of γ-chloropropylalkoxysilanes and ammonia is described in German Pat. No. 1,023,462, wherein it is stated that the reaction must take place at temperatures of at least 90° C. and under pressure. At 90° C., the pressure is approximately 57 bar and accordingly higher at even higher temperatures.

With large-scale applications of this prior art method, the relatively high pressure developing thereby is undesirable with respect to construction and design of the reactor.

However, since according to German Pat. No. 1,023,462 the reaction of γ-chloropropyltrialkoxysilanes and ammonia must take place at least at 90° C., it was to be expected that a reduction of the reaction temperature which necessarily effects a reduction in pressure, would significantly reduce the reaction speed which in turn reduces the volume-time yield of γ-aminopropyltrialkoxysilanes. Tests conducted by the applicant confirmed these anticipated theoretical results: a reduction of the temperature in the process according to German Pat. No. 1,023,462 under otherwise identical conditions leads to a reduced volume-time yield.

It is stated in German Pat. No. 1,023,462, that the yields of mono-(alkoxysilylpropyl)amine increase together with an increase of excess ammonia in relation to γ-chloropropylalkoxysilanes; however, according to the data given therein, the yield is approximately only 50% of the primary amines, even at a mol ratio of 20:1 of ammonia and γ-chloropropylalkoxysilane. The object was therefore for a large-scale production process to increase the yields of γ-aminopropylalkoxysilanes and to carry out the reaction at the lowest possible pressure.

This object was realized when a method of preparing γ-aminopropylalkoxysilanes of the formula

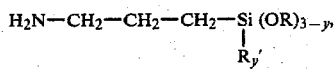

was found, wherein R is an alkyl moiety with 1 to 4 carbon atoms and R' can be the methyl or phenyl moiety and y=0 or 1 or 2, by reacting the corresponding γ-chloropropylalkoxysilanes with ammonia at increased temperatures and under pressure, wherein the reaction takes place by stirring the mixture at temperatures of between 60° and 90° C.

The process according to the invention permits the reaction to take place at temperatures below 90° C. and to obtain yields which are higher than those obtained at a reaction temperature of 100° C.

As in the method according to German Pat. No. 1,023,462, here too the ammonia is used primarily in liquid form in the pressure vessel (i.e. at more than 50 percent by weight), even if only about one fourth of the volume of the pressure vessel is filled with the liquid reaction products.

The reduction of pressure effected by the method according to the present invention during the reaction of γ-chloropropylalkoxysilanes and ammonia permits the use of pressure vessels with substantially thinner walls than those used in the prior art method. When the method according to German Pat. No. 1,023,462 is used for example in a 5 cubic meter pressure vessel and an accordingly large amount of ammonia is utilized at 100° C., the pressure vessel must have walls of a thickness of about 40 mm, whereas, on the same scale in the method according to the present invention, the required pressure apparatus will have walls of only about 26 mm thickness, depending on the design of the vessel.

In the process according to the invention, the pressure is generally maintained at below 40 bar and preferably within 30 and 35 bar. Thus, by using the method according to the invention as compared with the prior art processes, it is possible to reduce the reaction pressure by almost fifty percent without prolonging the reaction time.

The reaction mixture is stirred with any of the known stirring apparatus, such as flat blade agitators or impellers for example. There is very little influence on the yield by the speed at which the mixture is stirred, however, the speed must be sufficiently high to permit the reactants to be thoroughly mixed. Of course, the optimum stirring speed depends on the size and shape of the pressure vessel and the stirrer, and can be within the range of 50 to 600 rpm.

Advantageously, the reaction is carried out with a large excess of ammonia to reduce the development, known per se, of bis- or tris-trialkoxysilylamines. If mono-trialkoxysilylpropylamines should be primarily obtained, the molar ratio of ammonia and γ-chloropropylalkoxysilane must be at least 20:1, and is preferably between 30:1 and 80:1.

Contrary to the statements in German Pat. No. 1,023,462, it was surprisingly found that when the reaction mixture is stirred at the same time, the yields are at least as high even at temperatures of below 90° C. within the reaction time indicated in the patent. The reaction temperature is advantageously between 60° and 75° C., while the reaction is slower at temperatures of below 55° C. approximately. However, in principle it is possible to carry out the reaction according to the invention even at temperatures down to 50° C.

The γ-chloropropylalkoxysilanes used according to the invention are characterized by the general formula

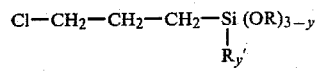

wherein R is an alkyl moiety with 1 to 4 carbon atoms and R' can be the methyl or phenyl moiety and y=0 or 1 or 2. Preferably, y=0 and R is a methyl or ethyl moiety.

In the reaction according to the invention, γ-aminopropylalkoxysilanes are primarily produced wherein the Cl-moiety of the starting product is replaced by an amino group. However, the known bis- or tris-(alkoxysilylpropyl)amines are byproducts which develop through the reaction of the aminopropylalkoxysilane with unreacted γ-chloropropylalkoxysilane, and the greater the excess of ammonia, the lower the percentage of these byproducts.

EXAMPLE 1 (Comparison example)

1,600 g of γ-chloropropyltriethoxysilane (6.64 mol) and 3,400 g of ammonia (200 mol) are filled into a 10-liter autoclave. The vessel is sealed and kept at a temperature of from 98° to 101° C. over a period of time of 12 hours, and a reaction pressure of 63 to 64 bar is reached. After 12 hours, the reaction vessel is cooled to 20° C. and the ammonia is slowly evaporated. Thereafter, the autoclave cover is removed, the reaction mixture is mixed with 1 liter of toluene and the ammonium chloride produced during the reaction is filtered off.

The purification of the filtrate by distillation yields 1,081 g of γ-aminopropyltriethoxysilane, thus, the yield is 73.5% with reference to the γ-chloropropyltriethoxysilane used.

EXAMPLE 1 b 1,600 g of γ-chloropropyltriethoxysilane (6.64 mol) and 3,400 g of liquid ammonia (200 mol) are filled into the 10-liter autoclave described in (a). The vessel is kept sealed and at a temperature of 75° C. for a period of 12 hours. The reaction pressure is 37 bar.

After 12 hours, the reaction mixture is processed further in the same manner as described in (a). 992 g of γ-aminopropyltriethoxysilane is obtained which is a yield of 67.5% in relation to the γ-chloropropyltriethoxysilane used.

EXAMPLE 2

In the autoclave of Example 1, the same amount of ammonia and γ-chloropropyltriethoxysilane as that used in Example 1 are reacted at a temperature of 75° C. The reaction time is shortened to 8.5 hours. The mixture of reactants is kept moving by a stirrer which turns at a speed of 585 rpm. The reaction pressure lies between 37 and 37.5 bar. After a reaction time of 8.5 hours, the reaction mixture is cooled and further treated analog to Example 1.

1,088 g of γ-aminopropyltriethoxysilane is obtained through fractionated distillation, which is a yield of 74.0% with respect to the γ-chloropropyltriethoxysilane used.

EXAMPLE 3

962 g of γ-chloropropyltriethoxysilane (4 mol) and 3,400 g of ammonia (200 mol) are filled into the 10-liter autoclave of Example 2. The vessel is sealed and a stirrer apparatus mixes the reactants at 585 rpm. The autoclave is kept at a temperature of 75° C. for a period of 8.5 hours. The reaction pressure is between 37 and 37.5 bar.

Further treatment of the reaction product according to the processes in Example 1 yields 698 g of γ-aminopropyltriethoxysilane (79%).

EXAMPLE 4 (Comparison example)

3,190 g of ammonia (187.5 mol) and 601 g of γ-chloropropyltriethoxysilane (2.5 mol) are filled into the 10-liter autoclave according to Example 1. After sealing the autoclave, it is heated to 100° C. and kept at this temperature for 8.5 hours. The reactant mixture is not stirred.

Further treatment according to Example 1 yields 409 g of γ-aminopropyltriethoxysilane (=74.0% of the theoretical yield). Although there was a large excess of ammonia, the yield obtained at such high temperature was not as good as that obtained at lower temperatures and with a lower excess of ammonia according to the invention (cf. Example 3).

EXAMPLE 5

426 kg of γ-chloropropyltriethoxysilane (1,771 mol) and 2,254 kg of ammonia (132,588 mol) are fed into a 5,000-liter autoclave. Thereafter, the autoclave is heated to 70° C. and the reaction pressure holds at about 38 bar. The reaction temperature of 70° C. is maintained over a period of time of 10 hours, while the reaction mixture is stirred with a stirrer apparatus at a rotational speed of 90 rpm.

Further treatment is according to Example 1, and 317 kg of γ-aminopropyltriethoxysilane is obtained which is a yield of 81%.

EXAMPLE 6

55 kg of γ-chloropropyltriethoxysilane (229 mol) and 194 kg ammonia (11,411 mol) are filled into an autoclave of a volume of 420 liter. The reactor is kept at a temperature of 63° to 65° C. for a period of time of 12 hours. The reactant mixture is stirred by a stirrer apparatus (at rotational speeds of about 85 rpm). During the reaction, a pressure of 28 bar is maintained.

The raw amine processing according to Example 1 yields 389 kg or 77% of γ-aminopropyltriethoxysilane.

What is claimed is:

1. In a method of preparing γ-aminopropylalkoxysilanes of the formula

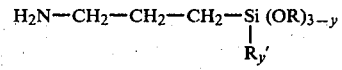

wherein R is an alkyl moiety with 1 to 4 carbon atoms and R' is the methyl or phenyl moiety and y=0 or 1 or 2, by reacting γ-chloropropylalkoxysilanes with ammonia at elevated temperatures and under pressure, the improvement wherein the reaction takes place while the mixture is stirred at temperatures of between 50° and 90° C.

2. A method according to claim 1 wherein the reaction is conducted at a temperature below 90° C.

3. A method according to claim 2 wherein the molar ratio of ammonia to gamma-chloropropyl alkoxy silane is at least 20:1.

4. A method according to claim 3 wherein the molar ratio of ammonia to gamma-chloropropyl alkoxy silane is 30-80:1.

5. A method according to claim 3 wherein the reaction temperature is between 60° and 75° C.

6. A method according to claim 1 wherein the reaction mixture is stirred with a stirrer at a rate of 50 to 600 rpm.

7. A method according to claim 1 wherein the silane reactant is gamma-chloropropyl triethoxy silane.

8. A method according to claim 1 wherein the pressure within the reaction vessel is below 40 bar.

9. A method according to claim 8 wherein the pressure within the reaction vessel is within 30 and 35 bar.

10. A method according to claim 1 wherein more than 50% of the ammonia is in liquid form.

* * * * *